(12) United States Patent
Stoll

(10) Patent No.: US 6,852,870 B2
(45) Date of Patent: Feb. 8, 2005

(54) OMEGA-3 FATTY ACIDS IN THE TREATMENT OF DEPRESSION

(75) Inventor: Andrew Stoll, 35 Old Winter St., Lincoln, MA (US) 01773

(73) Assignee: Andrew Stoll, Lincoln, MA (US)

( * ) Notice: Subject to any disclaimer, the term of this patent is extended or adjusted under 35 U.S.C. 154(b) by 143 days.

(21) Appl. No.: 10/083,913

(22) Filed: Feb. 27, 2002

(65) Prior Publication Data

US 2003/0012827 A1 Jan. 16, 2003

Related U.S. Application Data

(63) Continuation-in-part of application No. 10/068,035, filed on Feb. 5, 2002, which is a continuation of application No. 09/269,361, filed as application No. PCT/US97/06712 on Apr. 23, 1997, now Pat. No. 6,344,482.

(51) Int. Cl.$^7$ .................................................. C07F 9/02
(52) U.S. Cl. ........................ 554/79; 514/560; 514/642; 424/677; 424/722
(58) Field of Search ........................... 554/79; 514/560, 514/562; 424/722

(56) References Cited

U.S. PATENT DOCUMENTS

| | | | |
|---|---|---|---|
| 4,701,468 A | | 10/1987 | Mendy et al. ............... 514/547 |
| 5,252,333 A | * | 10/1993 | Horrobin ..................... 424/422 |
| 5,434,183 A | | 7/1995 | Larsson-Backström ..... 514/549 |

FOREIGN PATENT DOCUMENTS

| | | |
|---|---|---|
| EP | 0 289 204 A3 | 11/1988 |
| EP | 0 289 204 A2 | 11/1988 |
| WO | WO 94/28913 | 12/1994 |
| WO | WO 97/39759 | 10/1997 |

OTHER PUBLICATIONS

Invitation to Pay Additional Fee with a Communication Relating to the Results of the Partial International Search for PCT/US03/05926.
Adams, J., "Literature Review of Essential Fatty Acids", puterakembara.org, retrieved on Jul. 23, 2003.
Cohen, et al., "Lecithin in Mania: A Preliminary Report", Am J Psychiatry 137, 242–243, 1980.
Cohen, et al., "Lecithin in the Treatment of Mania: Double-–Blind Placebo–Controlled Trials", Am J Psychiatry 139, 1162–1164, 1982.
Dimmitt, S.B., "Recent Insights into Dietary Fats and Cardiovascular Disease", Clin. Exp. Pharmacol. Physiol. 22, 204–8, 1995 (abstract only).

Locke, et al., "Omega–3 Fatty Acids in Major Depression", World Review of Nutrition and Dietetics, 89: 173–185, 2001.
Maidment, I., "Are Fish Oils an Effective Therapy in Mental Illness—an Analysis of the Data", Acta Psychiatr Scand., 102: 3–11, 2000.
Mischoulon, et al., "Docosahexanoic Acid and ω–3 Fatty Acids in Depression", The Psychiatric Clinics of North America, 23(4): 785–794, 2000.
Puri, et., "The Effects of Olive Oil on ω3 Fatty Acids and Mood Disorders", Arch Gen Psychiatry 57, 2000.
Puri, et al., "Eicosapentaenoic Acid in Treatment–Resistant Depression", Archives of General Psychiatry, 59(1): 91–92, 2002.
Schreier, H., "Mania Responsive to Lecithin in a 13–Year–Old Girl", Am J Psychiatri 139, 108–110, 1982.
Sperling, R., "Dietary Omega–3 Fatty Acids: Effects on Lipid Mediators of Inflammation and Rheumatoid Arthritis", Rheumatic Disease Clinics of North America 17, 373–389, 1991.
Sperling, et al., "Dietary ω–3 Polyunsaturated Fatty Acids Inhibit Phosphoinositide Formation and Chemotaxis in Neutrophils", J. Clin. Invest 91, 651–660, 1993.
Stoll, et al., "Choline Ingestion Increases the Resonance of Choline–Containing Compounds in Human Brain: An In Vivo Proton Magnetic Resonance Study", Society of Biological Psychiatry 37, 170–174, 1995.
Stoll, et al., "Omega 3 Fatty Acids in Bipolar Disorder", Arch Gen. Psychiatry, 56: 407–412, 1999.
Stoll, et al., "Omega–3 Fatty Acids and Bipolar Disorder: A Review", Prostaglandins, Leukotrienes and Essential Fatty Acids, 60: 329–337, 1999.
Stoll, et al., "Methodological Considerations in Clinical Studies of ω3 Fatty Acids in Major Depression and Bipolar Disorder", World Review of Nutrition and Dietetics, 88: 58–67, 2001.

* cited by examiner

Primary Examiner—Deborah D. Carr
(74) Attorney, Agent, or Firm—Choate, Hall & Stewart; Valarie B. Rosen

(57) ABSTRACT

The present invention is directed to a method of treating patients with major depression by administering omega-3 fatty acids. These may be administered in a substantially purified form, as part of a pharmaceutical composition, or as part of a larger molecule, e.g., a triacylglycerol, which releases free fatty acid after ingestion by a patient.

The present invention is also directed to triacylglycerols which are esterified at the gamma cardon of glycerol to phosphocholine and at either the alpha or beta carbon of glycerol to an omega-3 fatty acid. These "omega-3 phoshatidylcholines" are also used in the treatment of patients with major depression.

16 Claims, No Drawings

OMEGA-3 FATTY ACIDS IN THE TREATMENT OF DEPRESSION

This application is a continuation-in-part of U.S. patent application Ser. No. 10/068,035, filed Feb. 5, 2002 entitled "Omega-3 Fatty Acids and Omega-3 Phosphatidylcholine in the Treatment of Bipolar Disorder", filed Feb. 5, 2002, using Express Mail No.: ET796587916US, which is a continuation of U.S. Ser. No. 09/269,361, filed Mar. 22, 1999, now issued as U.S. Pat. No. 6,344,482, which claims priority from PCT/US97/06712, filed Apr. 23, 1997. The contents of all of these applications are incorporated herein by reference.

FIELD OF THE INVENTION

The present invention relates to medical treatments for psychiatric disorders. More specifically, it is concerned with novel methods and compositions for treating patients with unipolar major depression.

BACKGROUND OF THE INVENTION

Major depression is a neuropsychiatric illness characterized by a persistently low mood or diminished interests in one's surroundings, accompanied by at least several of the following symptoms: Reduced energy and motivation, difficulty concentrating, altered sleep and appetite, and at times, suicidal ideation (American Psychiatric Association: *Diagnostic and Statistical Manual of Mental Disorders, ed. 4*. Washington, American Psychiatric Association, 1994). Major depression without a history of abnormally elevated mood and energy (mania) is termed "unipolar major depression." However, a sizeable proportion of depressed patients presenting for treatment have bipolar disorder (also known as manic depressive illness), where there is a history of mania, or a milder form of mood elevation known as hypomania (Goodwin F K, Jamison K R: *Manic Depressive Illness*. London, Oxford University Press, 1990). Whether part of a unipolar or a bipolar illness, major depression is associated with high rates of morbidity and mortality, with suicide rates of 10–25% (Kaplan H I, Sadock B J (eds): *Synopsis of Psychiatry*. Baltimore, Williams & Wilkins, 1998, p. 866). According to the World Health Organization (WHO), major depression is the fourth leading cause of vocational disability on earth (Murray C J L, Lopez A D (eds): *The Global Burden of Disease*. Geneva, World Health Organization, 1996, vol. 1). Furthermore, the incidence of major depression increased and the age of onset of depression decreased with each passing decade of the 20th century (Klerman G L, Weissman M M: Increasing rates of depression. *JAMA* 1989; 261:2229–2235). Effective psychotherapeutic and pharmacological antidepressant treatments for major depression exist, but each has shortcomings. Two modern forms of psychotherapy, cognitive-behavioral therapy and interpersonal therapy, have shown efficacy in controlled studies of major depression (Kaplan, 1998, pp. 885–931). However, for moderate or severe depression, antidepressant medication is generally more effective, rapidly acting, and less expensive than psychotherapy. The combination of psychotherapy and medications has recently been shown to be superior to either treatment modality (Keller M B, et al.: A comparison of nefazodone, the cognitive behavioral-analysis system of psychotherapy, and their combination for the treatment of chronic depression. *N Engl J Med* 2000; 342:1462–1470). There are more than 20 approved antidepressant drugs available in the United States. All of these medications have proven acute efficacy for major depression. The newer agents, such as the selective serotonin reuptake inhibitors (SSRIs), are far less toxic than the older classes of antidepressants, but even the SSRIs carry a substantial burden of side-effects, including sexual dysfunction, sleep disturbance, and weight gain (Kaplan, 1998). In addition, no currently available antidepressant is acutely effective in more than 60–70% of the patients who receive it. Furthermore, long-term data exists for only a few antidepressant drugs, and it appears that efficacy may diminish over time with some agents (Fredman S J, et al.: Partial response, nonresponse, and relapse with selective serotonin reuptake inhibitors in major depression: a survey of current "next-step" practices. *J Clin Psychiatry*; 2000, 61:403–408). Thus, there is a need for newer treatments, with greater efficacy and safety, as well as fewer side-effects.

SUMMARY OF THE INVENTION

A method has been developed for treating a human patient for unipolar major depression by administering omega-3 fatty acids at a dosage sufficient to reduce or eliminate its symptoms, i.e. at a dosage sufficient to reduce the frequency or lessen the severity of depression experienced by such patients. The most preferred omega-3 fatty acids are eicosapentanoic acid, docosahexanoic acid, and $\alpha$-linolenic acid. The fatty acids may be administered as the sole therapeutic agent or in conjunction with other agents known to be useful in the treatment of depression in patients. In particular, the fatty acids may be administered with an additional psychotropic medication. In addition, omega-3 fatty acids may be taken by patients as a component of another molecule, e.g. a triacylglycerol, and be metabolically released after ingestion.

The present invention is also directed to an omega-3 phosphatidylcholine useful in the treatment of unipolar major depression, consisting of glycerol esterified at both its $\alpha$ and $\beta$ carbons to fatty acids. At least one, and preferably both, of these fatty acids is an omega-3 fatty acid, and the position of the glycerol should be esterified to phosphocholine. It is preferred that at least one of the esterified fatty acids be eicosapentanoic acid, docosahexanoic acid, or $\alpha$-linolenic acid. Omega-3 phosphatidylcholines with eicosapentanoic acid esterified to the carbon and docosahexanoic acid esterified to the $\beta$ carbon, or vice versa, are the most preferred. In all cases, the position of the triacylglycerol is esterified to phosphocholine.

DETAILED DESCRIPTION OF THE INVENTION

In the following description, reference will be made to various methodologies well-known to those skilled in the art of medicine and pharmacology. Such methodologies are described in standard reference works setting forth the general principals of these disciplines. Included among the relevant references are: Goodwin, F. K. and Jamison, K. R., *Manic Depressive Illness*, Oxford University Press (1990); and Bloom, F. and Kupfer, D., *Psychopharmacology. The Fourth Generation of Progress*, Raven Press (1994).

A. Definitions

Major Depression: Major depression is characterized by two or more weeks of predominantly low mood or diminished interest in one's usual activities combined with four or more of the following symptoms: sleep alteration (either increased or decreased), inappropriate guilt or loss of self-esteem, altered appetite (either increased or decreased), diminished energy, diminished concentration, psychomotor symptoms (either agitation or retardation), and suicidal ideation.

Omega-3 fatty acids: Fatty acids are long chain polyunsaturated molecules beginning with a methyl group and ending with a carboxyl group. Omega-3 fatty acids contain a double bond in the third position from the methyl group. Two common, long chain omega-3 fatty acids are eicosapentanoic acid (20 carbons in length) and docosahexanoic acid (22 carbons in length). These are both found in fish oils Triacylglycerol: Compounds in which the carboxyl groups of fatty acids are esterified to the hydroxyls of all three carbons found in glycerol are referred to as triacylglycerols or triglycerides. Triacylglycerols in which the terminal carbon of glycerol (the "γ carbon") is esterified to phosphocholine are called phosphatidylcholines. The next carbon in the glycerol is referred to herein as the "β carbon," and the following carbon is referred to as the "α carbon."

Omega-3 phosphatidylcholine: As used herein the term "omega-3 phosphatidylcholine" refers to a triacylglycerol in which the γ carbon of glycerol is esterified to phosphocholine, and at least one of the other carbons of glycerol is esterified to an omega-3 fatty acid.

Choline: Choline (hydroxyethyl trimethyl ammonium hydroxide) is considered to be a vitamin of the B complex and is derivable from many foods. Unless otherwise indicated, the term "choline" as used herein, refers not only to the isolated choline molecule (i.e. free choline) but also to any biologically compatible salt of choline (e.g., choline bitartrate).

Lithium: Unless otherwise indicated, the term "lithium" refers to any salt containing lithium as the cationic component.

Unipolar Major Depression: Unipolar major depression is a mood disorder in which patients suffer from one or more episodes of major depression.

B. Background

Omega-3 fatty acids have been linked to the etiology, pathophysiology, and treatment of unipolar major depression. Six lines of evidence support a role for the omega-3 fatty acids in major depression. First, there are compelling epidemiological hypotheses and data linking low omega-3 fatty acid intake with high rates of major depression (Smith R S: The macrophage theory of depression. *Med Hypotheses*; 1991, 35:298–306; Rudin D O: The major psychoses and neuroses as omega-3 essential fatty acid deficiency syndrome: substrate pellagra. *Biol Psychiatry*; 1981, 16:837–850; Hibbeln J R, Salem N: Dietary polyunsaturated fats and depression: when cholesterol does not satisfy. *Am J Clin Nutr*; 1995, 62:1–9; Hibbeln J R: Fish consumption and major depression. *Lancet*; 1998, 351:1213). For example, Hibbeln reported his findings of a very strong relationship between the per capita amount of fish a given country consumes and the rates of major depression within that country (Hibbeln, 1998). The second and third lines of evidence involve neurochemical studies of omega-3 fatty acid function in animals and biochemical analyses of the omega-3 content of blood of patients with major depression, respectively (Delion S, et al.: Alpha-Linolenic acid dietary deficiency alters age-related changes of dopaminergic and serotonergic neurotransmission in the rat frontal cortex. *J Neurochem*; 1996, 66(4):1582–91; Chalon S, et al.: Dietary fish oil affects monoaminergic neurotransmission and behavior in rats. *J Nutr* 1998; 128(2):2512–9; Heron D S, et al.: Lipid fluidity markedly modulates the binding of serotonin to mouse brain membranes. *Proc Natl Acad Sci, USA*; 1980, 77:7463–7467; Adams P B, et al.: Arachadonic acid to eicosapentaenoic acid ratio in blood correlates positively with clinical symptoms of depression. *Lipids*; 1996, 31 suppl: S157–S161; Maes M, et al.: Fatty acid composition in major depression: decreased omega-3 fractions in cholesteryl esters and increased C20:4 omega 6/C20:5 omega 3 ratio in cholysteryl esters and phospholipids. *J Affect Disord*; 1996, 38:35–46; Peet M, et al.: Omega-3 polyunsaturated fatty acid levels in the diet and in red blood cell membranes of depressed patients. *J Aff Disorders*; 1998, 48:149–55). The omega-3 fatty acids have fundamental structural and functional roles in the developing and mature nervous system (Uauy R, et al.: Role of essential fatty acids in the function of the developing nervous system. *Lipids*; 1996, 31:S167–S176; Bourre J M, et al.: Function of dietary polyunsaturated fatty acids in the nervous system. *Prostaglandins Leukotrienes and Essential Fatty Acids*; 1993, 48: 5–15). The fourth line of evidence points to the presence of abnormalities in the EPA dependant eicosanoid and cytokine pathways in the brain during major depression (Smith, R S, 1991; Maes M, et al.: Significantly increases expression of T-cell activation markers (interleukin-2 and HLA-DR) in depression: further evidence for an inflammatory process during that illness. *Prog Neuropsychopharmacol Biol Psychiat*; 1993, 17:241–255; Maes M: Evidence for an immune response in major depression: a review and hypotheses. *Prog Neuropsychopharmacol & Biol Psychiat*; 1995, 19:11–38). The fifth line of evidence is the strong antidepressant effect of the omega-3 fatty acids observed a recent double-blind, placebo-controlled study in bipolar disorder (Stoll A L, et al.: Omega-3 fatty acids in bipolar disorder: a preliminary double-blind, placebo-controlled trial. *Archives Gen Psychiatry*; 1999, 56:407–412). This study is relevant because all compounds with antidepressant effects in bipolar disorder will exhibit antidepressant effects in unipolar depression. The final line of evidence involves preliminary uncontrolled open-label clinical studies reporting mood elevating effects of the omega-3 fatty acids in patients with unipolar depression and other neuropsychiatric disorders (Rudin, 1981; Stoll A L, et al.: Omega-3 fatty acids and bipolar disorder: a review. *Prostaglandins, Leukotrienes, and Essential Fatty Acids*; 1999, 60:329–37).

Omega-6 fatty acids (particularly arachidonic acid, or AA) are generally antagonistic to omega-3 (EPA) action in the immune and inflammatory systems (Lands WEM: Biochemistry and physiology of n-3 fatty acids. *FASEB J*; 1992, 6:2530–2536). Unlike omega-3 fatty acids, omega-6 fatty acids are ubiquitous in developed countries. Omega-6 fatty acids are derived from seed and vegetable oils that have increased in our diet through the incorporation of these oils by the food industry—at the recommendation of the American Heart Association and others (Report of the Dietary Guidelines Advisory Committee on the Dietary Guidelines for Americans. *In: Dietary Guidelines for Americans*; Washington, D.C. US Dept of Health and Human Services; 2000). There is indirect evidence that the optimal dietary ratio of omega-6 to omega-3 fatty acids should be close to 1:1, and under these optimal conditions, the omega-6 fatty acid AA competes with the omega-3 fatty acid EPA to achieve balanced immune and inflammatory function (Leaf A, Weber P C: A new era for science in nutrition. *Am J Clin Nutr*; 1987, 45:1048–1053; Eaton S B: Humans, lipids and evolution. *Lipids*; 1992, 27:814–820; Simopoulos AP, et al.: Workshop on the essentiality of an recommended dietary intakes for omega-6 and omega-3 fatty acids. *J Am Coll Nutr*; 1999, 18:487–489, Lands, 1992). Like EPA, AA is converted to a series of eicosanoids, including the prostaglandins and leukotrienes, which have an important role in regulating leukocyte cytokine production and release. Landes has reported that the eicosanoids from arachidonic acid are synthesized in an intense and rapid manner, and likewise have intense and powerful actions in the body (Lands, 1992). Eicosanoids derived from the omega-3 fatty acid EPA are created more slowly and their actions are often moderate in comparison to the omega-6 derived eicosanoids. EPA and AA are intended to be in balance, and without sufficient EPA, AA and its progeny will monopolize eicosanoid-associated systems throughout the body, increasing the risk for intense, unchecked inflammatory responses. Such an imbalance towards the omega-6 eicosanoids causes white blood cells to release potent immune activating cytokines, which can adversely affect health if chronically or abnormally activated. Likewise, EPA can dramatically check this AA driven process at several levels, including direct inhibition of the eicosanoid producing enzyme cyclooxygenase-2 (Obata T, et al.: Eicosapentaenoic acid inhibits prostaglandin D2 generation by inhibiting cyclooxygenase-2 in cultured human nast cells. *Clin Exp Allergy*; 1999, 2:1129–1135).

In collaboration with Baylor College of Medicine, a 2-site study designed to examine the efficacy of omega-3 fatty acids in patients with unstable bipolar disorder was performed (Stoll, 1999). The study was performed to confirm the hypothesis that one could discover new mood agents by searching the medical literature for compounds with biochemical actions similar to currently used medications. The omega-3 fatty acids shared characteristics with lithium, valproate, and even the SSRI class of antidepressants. This pilot study was a 4-month, prospective, double-blind, parallel design, placebo-controlled trial, comparing the efficacy of high dose omega-3 fatty acids from fish oil (9.6 grams per day) vs. placebo (olive oil) in bipolar patients who had experienced a recent mania or hypomania.

The study was originally intended to run 9 months per patient. However, the study was terminated after a pre-planned interim data analysis at the 4-month mark revealed marked differences between the omega-3 fatty acid and placebo groups. In nearly every outcome measure, the omega-3 fatty acid group performed better than the placebo group. Nine of 14 (64.3%) patients treated with omega-3 fatty acids responded to treatment, compared to 3 of 16 (18.8%) placebo-treated subjects (p=0.02; Fisher). The omega-3 fatty acids in this study demonstrated mood stabilizing activity. However, the most robust finding was the strong antidepressant effects of the omega-3 fatty acids in this group of bipolar patients.

In 1981, Rudin, published an open-label case-series on the use of high dosages of flaxseed oil in psychiatric patients with a variety of diagnoses (Rudin, 1981). He noted antidepressant effects, as well as a frequent occurrence of mania, presumably induced by the large dosage of α-linolenic acid used. In terms of other uncontrolled data, the authors have previously described treating 16 patients with treatment-refractory unipolar major depression with omega-3 fatty acids (Stoll, 1999). Five of the 16 patients responded at least partially, while 4 of the 5 responders had a marked response to the addition of omega-3 oils to their ongoing antidepressant treatment. Although 5 of 16 (31%) may seem like a low rate of response to a treatment, it is important to keep in mind that patients with treatment-resistant depression often have response rates well below this figure.

Several compelling and independent lines of evidence support a role for the omega-3 fatty acids in the etiology, pathogenesis, and the treatment of unipolar major depression. Historically, DHA has been the major focus of many investigators due to its large structural role in the brain. However, EPA is involved in a huge array of neuropsychiatrically relevant biochemical processes, and the bulk of the biochemical data in patients with unipolar depression indicates that EPA depletion is more highly correlated with depression severity than the other omega-3 fatty acids. There are also preliminary indications that α-linolenic acid may also possess antidepressant action.

C. Method of Treating Patients For Major Depression Using Omega-3 Fatty Acids

The present invention is directed to a method for treating human patients for unipolar major depression by administering omega-3 fatty acids. Although the method is not restricted to any one particular type of omega-3 fatty acid, it is preferred that eicosapentanoic acid (EPA) or docosahexanoic acid (DHA) be used. Both EPA and DHA are found in a variety of fish oils and are commercially available in an essentially pure form.

Dosage

The total daily dosage of omega-3 fatty acid administered to a human patient should be at least the amount required to reduce or eliminate the symptoms associated with major depression. Specifically, the dosage should be high enough to either reduce the severity of the depressive episodes experienced by patients or decrease the frequency at which such episodes occur. Physicians may begin by administering relatively small doses of omega-3 fatty acid (e.g. 1 gram per day) and then adjust the dosage upward as it becomes clear that the patient can tolerate the treatment. The final daily dosage should be between 1 and 30 grams of fatty acid per day, with typical doses ranging between 2 and 10 grams per day. Dosages may be provided in either a single or multiple dosage regiment.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In many cases, a patient will already be taking medications for the treatment of major depression at the time that treatment with omega-3 fatty acid is initiated. In addition, patients may be taking medications for other diseases or conditions. The other medications may be continued during the time that omega-3 fatty acid is given to the patient, but it is particularly advisable in such cases to begin with low doses to determine if adverse side effects are experienced.

Dosage Forms and Route of Administration

The present invention is not limited to any particular dosage form or route of administration. Oral administration will generally be most convenient; however, the invention is compatible with parenteral, transdermal, sublingual, buccal or implantable routes of administration as well.

Omega-3 fatty acids may be given in a substantially purified form or as part of a pharmaceutical composition containing one or more excipients or flavoring agents. Compositions may also include psychotropic medications, including lithium, antidepressants, anticonvulsants, mood stabilizers, antipsychotic agents, and benzodiazepines. Preparations may be solid or liquid and take any of the pharmaceutical forms presently used in human medicine, e.g. tablets, gel capsules, granules, suppositories, transdermal compositions or injectable preparations.

The active ingredient or ingredients may be incorporated into dosage forms in conjunction with any of the vehicles which are commonly employed in pharmaceutical preparations, e.g. talc, gum arabic, lactose, starch, magnesium searate, cocoa butter, aqueous or non-aqueous solvents, oils, paraffin derivatives or glycols. Emulsions such as those described in U.S. Pat. No. 5,434,183, may also be used in which vegetable oil (e.g., soybean oil or safflower oil), emulsifying agent (e.g., egg yolk phospholipid) and water are combined with glycerol. Fatty acids may be incorporated into preparations either in the form of the free acid or as a pharmaceutically acceptable salt. Methods for preparing appropriate formulations are well known in the art (see e.g., *Remington's Pharmaceutical Sciences,* 16th Ed., 1980, A. Oslo Ed., Easton, Pa.).

Manner of Treatment

In order to determine the effect of administered omega-3 fatty acid on mood alteration, patients should be evaluated on a regular basis over an extended period of time, e.g. 1 to 8 weeks. One good manner of carrying out evaluations is for patients to keep a daily diary in which they chart their moods. For example, patients may keep a daily record in which they rate their best and worst moods as either normal, mildly, moderately or severely depressed. These records should help the patient and their physician determine if depression occurs less frequently or becomes less extreme in intensity. Ideally, such a diary should be kept both before and after the administration of omega-3 fatty acid is begun. The evaluation of mood alterations by the patient should also be supplemented with periodic clinical evaluations carried out by a physician.

In some cases, the evaluation discussed above may indicate that mood fluctuations have become so stabilized in a patient as the result of administering omega-3 fatty acid at the initial concentration that no further adjustment in dosage is necessary. In other cases, the dosage of omega-3 fatty acid may be increased in order to obtain a more efficacious result. In general, dosage should not be increased beyond the point at which further stabilization of patient mood is observed. If adverse side effects are experienced by patients, then dosages may be adjusted in a downward direction accordingly.

The process of adjusting dosage in an upward or downward direction and evaluating the effect of the adjustment on mood changes should be continued until an optimum dosage is discovered, i.e. the dosage at which the patient experiences the best balance between therapeutic effectiveness and discomfort due to side effects. In cases where adverse side effects are not experienced, the optimal dosage is the lowest dose resulting in maximum reduction in depressive episodes.

Omega-3 fatty acids may be used in combination with other psychotropic agents including, for example, lithium, pharmaceutical antidepressants, herbal antidepressants (e.g., St. John's Wort, S-adenosylmethionine), anti-convulsants, mood stabilizers, antipsychotic agents, and benzodiazepines. These other agents may either be given together with omega-3 fatty acid in a single dosage form, or they may be administered separately.

Patients taking anti-depressants should continue taking the drug during the time at which omega-3 fatty acid treatment is begun. Optimal dosages for each of the drugs may then be determined sequentially. For example, administration of one agent may be initiated and then optimized followed by the initiation and optimization of omega-3 fatty acid treatment. The problem of adjusting the dosages of multiple therapeutic agents is one that is routinely encountered by physicians and can be solved using well-established procedures similar to those discussed herein.

Kits

Individual preparations containing omega-3 fatty acid and other therapeutic agents for major depression, such as choline or lithium, may be provided in the form of a kit, comprising a carrier (e.g. a box or bag) compartmentalized to receive one or more components (bottles, vials, packets, etc.) in close confinement. Such a kit will be carried by patients with major depression and will typically contain written instructions concerning the way in which the enclosed drugs should be taken, potential side effects, etc. The kit should be portable, and be generally convenient for use by patients.

D. Omega-3 Phosphatidylcholines

The present invention is also directed to omega-3 phosphatidylcholines in which glycerol is esterified at its $\gamma$ carbon to phosphocholine and at least one of the fatty acids esterified to either the $\alpha$ or $\beta$ carbons is an omega-3 fatty acid. It is preferred that both the $\alpha$ carbon and $\beta$ carbon of glycerol be esterified to an omega-3 fatty acid, with the preferred fatty acids being EPA and DHA. The most preferred phosphatidylcholines contain both DHA and EPA, one esterified at the $\alpha$ carbon of glycerol and the other at the $\beta$ carbon.

The phosphatidylcholines of the present invention may be synthesized using standard techniques well known in the art, see e.g. U.S. Pat. No. 4,701,468. One suitable method is to synthesize the "omega-3 phosphatidylcholines" from commercially available precursor lyso-phosphatidylcholines. Specifically, a lyso-phosphatidylcholine is acylated by combining the desired omega-3 fatty acid anhydride (e.g. from EPA or DHA) and 4-pyrrolidinopyridine as a catalyst (1.2 equivalents) in alcohol-free chloroform. Depending on the reaction conditions and the relative proportions of fatty acid, several different omega-3 phosphatidylcholine species will be generated. Using EPA and DHA, four major species will occur: dieicosapentanoylphosphatidylcholine, didocosahexanoylphosphatidylcholine, 1-eicosapentanoyl, 2-docosahexanoylphosphatidylcholine, and 1-docosahexanoyl, 2-eicosapentanoylphosphatidylcholine. The specific phosphatidylcholines of interest may then be isolated by well-established chromatographic methods.

E. Method of Treating Bipolar Disorder Using Omega-3 Phosphatidylcholines

The omega-3 phosphatidylcholines described above may be used for treating humans with unipolar major depression in the same manner and following the same procedures as those discussed in connection with omega-3 fatty acids. The phosphatidylcholines may be given in a substantially purified form or as part of a pharmaceutical composition. It is expected that optimized dosages will have sufficient omega-3 phosphatidylcholine to deliver between about one and about 30 grams of free omega-3 fatty acid per day, with the preferred daily dose being between 1 and 10 grams. Patients should keep diaries of daily mood fluctuations and be evaluated by a physician on a regular basis to determine the effect of treatment. Based upon such evaluations, dosages may be increased or decreased as needed.

As with omega-3 fatty acids, the omega-3 phosphatidylcholines may be delivered by any route and are compatible with any dosage form. Oral dosage forms such as tablets, capsules, powder packets and liquid solutions will generally be preferred. Therapeutically inert agents may be added to improve the palatability of preparations, and additional therapeutic agents may be included.

In cases where parenteral administration is elected as the route of administration, preparations containing omega-3 phosphatidylcholine may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

Omega-3 phosphatidylcholine and other psychotropic agents, e.g., lithium, antidepressants, anticonvulsants, mood stabilizers, antipsychotic agents, and beneodiazepines, may be provided as separate components in the form of a kit designed to be carried and used by patients. The kit would contain written instructions concerning the way in which the enclosed agents should be taken and other pertinent information.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. An omega-3 phosphatidylcholine useful in the treatment of unipolar major depression consisting of glycerol, wherein:
   a) the α and β carbons of said glycerol are both esterified to a fatty acid, at least one of which is an omega-3 fatty acid; and
   b) the γ carbon of said glycerol is esterified to phosphocholine.

2. The omega-3 phosphatidylcholine of claim 1, wherein both the α and β carbons of said glycerol are esterified to an omega-3 fatty acid.

3. The omega-3 phosphatidylcholine of either claim 1 or 2, wherein eicosapentanoic acid is esterified to a member of the α carbon, the β carbon, and both the α and β carbons of said glycerol.

4. The omega-3 phosphatidylcholine of either claim 1 or 2, wherein docosahexanoic acid is esterified to a member of the α carbon, the β carbon, and both the α and β carbons of said glycerol.

5. The omega-3 phosphatidylcholine of either claim 1 or 2, wherein alpha-linolenic acid is esterified to a member of the α carbon, the β carbon, and both the α and β carbons of said glycerol.

6. The omega-3 phosphatidylcholine of claim 1, wherein eicosapentanoic acid is esterified to the α carbon of said glycerol and docosahexanoic acid is esterified to the β carbon of said glycerol.

7. The omega-3 phosphatidylcholine of claim 1, wherein docosahexanoic acid is esterified to the αcarbon of said glycerol and eicosapentanoic acid is esterified to the β carbon of said omega-3 phosphatidylcholine.

8. A pharmaceutical composition comprising the omega-3 phosphatidylcholine of claim 1, wherein one or more unit doses of said composition provides an amount of said omega-3 phosphatidylcholine sufficient to reduce or eliminate the symptoms of unipolar major depression.

9. The pharmaceutical composition of claim 7, further comprising a member of lithium, a pharmaceutical antidepressant, an herbal antidepressant, an anticonvulsant, a mood stabilizer, an antipsychotic agent, and a benzodiazepine.

10. A method of treating unipolar major depression in a human patient, comprising administering the omega-3 phosphatidylcholine of claim 1 to said patient at a dose sufficient to reduce or eliminate the symptoms of unipolar major depression.

11. The method of claim 10, further comprising administering a pharmaceutically effective dose of at least one member of lithium, a pharmaceutical antidepressant, an herbal antidepressant, an anticonvulsant, a mood stabilizer, an antipsychotic agent, and a benzodiazepine.

12. A kit comprising a carrier containing in close confinement therein, none or more components wherein:
   a) a first component contains an omega-3 phosphatidylcholine; and
   b) a second component contains a psychotropic agent useful in the treatment of unipolar major depression.

13. The kit of claim 12, wherein the α carbon of said glycerol is esterified to eicosapentanoic acid and the β carbon of said glycerol is a esterified to doocosa-hexanoic acid.

14. The kit of claim 12, wherein the α carbon of said glycerol is esterified to docosahexanoic acid and the β carbon of said glycerol is a esterified to eicosapentanoic acid.

15. The kit of claim 12, wherein a member of eicosapentanoic acid, docosapentanoic acid, and alpha-linolenic acid is esterified to a member of the α carbon, the β carbon, and both the α and β carbons of said glycerol.

16. The kit of any one of claims 12–15, wherein said second component is selected from the group consisting of lithium, pharmaceutical antidepressant, an herbal antidepressant, an anticonvulsant, a mood stabilizer, an antipsychotic agent, and a benzodiazepine.

* * * * *